United States Patent [19]

Knight et al.

[11] 4,425,429

[45] Jan. 10, 1984

[54] COMPOSITION OF MATTER AND PROCESS

[75] Inventors: John C. Knight; Merle G. Wovcha, both of Kalamazoo, Mich.

[73] Assignee: The Upjohn Company, Kalamazoo, Mich.

[21] Appl. No.: 286,308

[22] Filed: Jul. 24, 1981

[51] Int. Cl.$^3$ ...................... C12P 33/16; C12P 33/06; C12R 1/33
[52] U.S. Cl. ....................................... 435/55; 435/58; 435/865
[58] Field of Search .................. 435/55, 58, 865, 863, 435/822, 830, 832, 840, 843, 872, 880, 886

[56] References Cited

U.S. PATENT DOCUMENTS

| | | | |
|---|---|---|---|
| 4,029,549 | 6/1977 | Antosz et al. | 435/55 |
| 4,035,236 | 7/1977 | Wovcha | 435/55 |
| 4,175,006 | 11/1979 | Wovcha et al. | 435/865 |
| 4,214,051 | 7/1980 | Wovcha et al. | 435/55 |

FOREIGN PATENT DOCUMENTS 79104372.2 of 0000 European Pat. Off. .

*Primary Examiner*—Esther M. Kepplinger
*Attorney, Agent, or Firm*—Roman Saliwanchik

[57] ABSTRACT

The subject invention concerns a novel fermentation process for making the novel useful steroid intermediate 9-hydroxy-3-oxo-4,17(20)-pregnadiene-20-carboxyaldehyde (I). This compound can be used as in the synthesis of valuable corticoids.

5 Claims, No Drawings

COMPOSITION OF MATTER AND PROCESS

DESCRIPTION

BACKGROUND OF THE INVENTION

U.S. Pat. No. 4,029,549 discloses and claims the use of *Mycobacterium fortuitum* NRRL B-8119 to make 9-hydroxy-3-oxo-4-pregnene-20-carboxylic acid [9-hydroxybisnoracid]. The same microbe is used to make 9-hydroxy-4-androstene-3,17-dione [9-hydroxyandrostenedione] in U.S. Pat. No. 4,035,236; and 9-hydroxy-3-oxo-4-pregnene-20-carboxylic acid methyl ester [9-hydroxybisnoracid methyl ester] in U.S. Pat. No. 4,214,051.

European Patent Application No. 79104372.2 discloses a two-stage fermentation for preparing 9-hydroxy-3-oxo-4,17(20)-pregnadiene-20-carboxylic acid (I) which is useful as an intermediate in the synthesis of valuable corticoids. This process entails first the conversion of sterols to 3-oxo-4,17(20)-pregnadiene-20-carboxylic acid by fermentation with Mycobacterium strain NRRL B-8054, and then conversion of this compound to (I) by incubation with any one of several microorganisms capable of introducing a hydroxyl group in the 9α position.

BRIEF SUMMARY OF THE INVENTION

Disclosed and claimed is a fermentation process for preparing the novel useful intermediate 9-hydroxy-3-oxo-4,17(20)-pregnadiene-20-carboxaldehyde (I). See Chart I. This process is conducted by use of a mutant of *M. fortuitum* NRRL B-8119. The subject invention process also encompasses the use of double mutants obtained from the genera of microorganisms disclosed in U.S. Pat. No. 4,029,549, i.e., Arthrobacter, Bacillus, Brevibacterium, Corynebacterium, Microbacterium, Mycobacterium, Nocardia, Protaminobacter, Serratia, and Streptomyces. The microorganisms of these genera are all well known sterol degraders. The wild type strains of these genera degrade sterols non-selectively to small molecular weight compounds, e.g. $CO_2 + H_2O$. Mutants can be made from these wild types by following the procedures disclosed in U.S. Pat. No. 4,029,549, Example 1. This example discloses the preparation of *M. fortuitum* NRRL B-8119.

Mutants of the genera disclosed above which can be made by using the procedures of Example 1 of U.S. Pat. No. 4,029,549, can then be subjected to the mutation procedures, disclosed herein, to prepare further mutants. These latter mutants, as exemplified here by *M. fortuitum* NRRL B-12433, can be used in the fermentation process, disclosed herein, to prepare compound (I).

DETAILED DESCRIPTION OF THE INVENTION

The Microorganisms

Mutants which are characterized by their ability to selectively degrade steroids having 17-alkyl side chains and accumulate 9-hydroxy-3-oxo-4,17(20)-pregnadiene-20-carboxaldehyde (I) as a major product in the fermentation beer can be obtained by mutating microorganisms of the following genera: Arthrobacter, Bacillus, Brevibacterium, Corynebacterium, Microbacterium, Mycobacterium, Nocardia, Protaminobacter, Serratia, and Streptomyces.

Following is an example of the preparation of the mutant used in the fermentation process. The mutant prepared in this example is *M. fortuitum* NRRL B-12433. Similar mutants from other Mycobacterium species and other microbe genera, as recited herein, can be prepared by following the procedures of the following example.

Preparation of a Mutant Which Accumulates 9-hydroxy-3-oxo-4,17(20)-pregnadiene-20-carboxaldehyde as a Major Product of the Degradation of Sterols

*Mycobacterium fortuitum* NRRL B-8119 is grown at 31° in a medium consisting of (per liter) nutrient broth, 8 g; yeast extract, 1 g; glycerol, 5 g; Tween 80, 0.1% (w/v); and distilled $H_2O$. This medium is sterilized by autoclaving at 15 lb/in$^2$ for 20 min. The cells are grown to a density of about $5 \times 10^8$ per ml, and then collected on a sterile 0.2 micron filter. The cells are washed with an equal volume of sterile 0.1 M sodium citrate, pH 5.6 containing 0.1% Tween 80, and then resuspended in ½ volume of the same buffer. N-methyl-N'-nitro-N-nitrosoguanidine is added to a concentration of 100 μg/ml and the cell suspension is incubated at 31° C. for 1 hr. The cells are then washed with 2 volumes of sterile 0.1 M potassium phosphate buffer, pH 7 containing 0.1% Tween 80, and then resuspended in 1 volume of the same buffer. A medium is prepared containing (per liter) nutrient broth, 8 g; NaCl, 5 g; glycerol, 5 g; and distilled $H_2O$. Agar is added to 15 g/l and the medium is autoclaved at 15 lb/in$^2$ for 20 min and then poured into sterile Petri dishes. The mutagenized cells are then plated on this medium and colonies which grow on these plates are subsequently screened in small scale fermentations for their ability to convert sterols to compound (I). Detection of the desired compound is by thin layer chromatography of methylene chloride extracts of the test fermentations, using silica gel and the solvent system methylene chloride-acetone-acetic acid (212-38-1). In this manner, mutant NRRL B-12433 is isolated which accumulates 9-hydroxy-3-oxo-4,17(20)-pregnadiene-20-carboxaldehyde as a major product of the bioconversion of sterols.

The key to isolating a mutant like the one described herein is to start with a mutant, such as NRRL B-8119, which is already blocked in steroid ring degradation so that it produces 9α-hydroxyandrostenedione, and introduce into this microorganism a second mutation affecting sterol side chain degradation.

Description of the Microorganism

The mutant bringing about the biotransformation described herein differs from its parent culture, e.g., *Mycobacterium fortuitum* NRRL B-8119, only in its action on steroid molecules. In all other respects, such as morphology and drug sensitivities, they are similar if not identical. Both *M fortuitum* cultures are acid-fast non-motile, non-sporulating bacilli belonging to the family Mycobacteriaceae of the order Actinomycetales. According to Runyon's classification, Runyon, E. H., 1959 Med. Clin. North America 43:273, it is a non-chromogenic group IV mycobacterium, i.e., it grows rapidly at low temperature to produce nonpigmented colonies on relatively simple media.

*M. fortuitum* NRRL B-8119 and NRRL B-12433 have been deposited in the permanent collection at the Northern Regional Research Laboratory, U.S. Department of Agriculture, Peoria, Ill., U.S.A. *M. fortuitum* NRRL B-8119 has been available to the public at least since issuance of the above-mentioned U.S. patents disclosing the microbe. *M. fortuitum* NRRL B-12433 was deposited on May 4, 1981. Subcultures of these microorganisms are available from the NRRL depository by request made thereto. It should be understood that the availability of the culture does not constitute a license to practice the subject invention in derogation of patent rights granted with the subject instrument by governmental action.

Compound (I) is useful as an intermediate in the synthesis of valuable corticoids. For example, it can be oxidized to the corresponding acid, i.e., 9-hydroxy-3-oxo-4,17(20)-pregnadiene-20-carboxylic acid, which in turn can be converted to hydrocortisone acetate by following the procedure detailed in published European Patent Application No. 79104372.2.

Following are examples which illustrate the fermentation process of the subject invention. These examples are merely illustrative, and, thus, should not be construed as limiting. All percentages are by weight and all solvent mixture proportions are by volume unless otherwise noted.

EXAMPLE 1

Fermentation of Crude Sitosterol

The biotransformation medium contains (per liter) Ucon, 8.0 g; Cerelose, 5.0 g; $NH_4Cl$, 3.0 g; $CaCO_3$, 3.0 g; $Na_3$[citrate].$2H_2O$, 3.0 g; Tween 80, 2.0 g; soyflour, 1.0 g; $KH_2PO_4$, 0.5 g; urea, 0.5 g and crude sitosterol, 30.0 g in tap water with the pH adjusted to 7.0. Flasks containing 100 ml portions of this medium are inoculated with 10 ml of seed cultures of *M. fortuitum* NRRL B-12433, grown at 28° in a medium containing (per liter) nutrient broth, 8.0 g; glycerol, 5.0 g; yeast extract, 1.0 g and Tween 80, 1.0 g in distilled water with the pH adjusted to 7.0. The cultures are then incubated at 28° for 336 hr on a rotary shaker. Following incubation, the mixture is extracted and the product isolated as detailed below in Example 3.

EXAMPLE 2

Just as in Example 1, but with various steroidal substrates provided singly or in combination and in pure or crude form. Such substrates include sitosterol, cholesterol, stigmasterol and campesterol.

EXAMPLE 3

Isolation of (I) from *M. fortuitum* NRRL B-12433 Fermentation

Fermentation beer (1200 ml) from a sitosterol bioconversion using *M. fortuitum* NRRL B-12433 is acidified and extracted twice with an equal volume of methylene chloride ($MeCl_2$), giving 29.2 g and 8.9 g crude extract respectively.

The first extract is redissolved in $MeCl_2$ and washed with saturated sodium bicarbonate solution to remove acidic components. The remaining neutral components are obtained as a brown oil (18.6 g) on removal of the solvent. It is shown by tlc and liquid chromatography to contain three principal uv-absorbing zones. The least polar of these is a mixture of the methyl esters A and B in which B predominates. See Chart I. The most polar is the 9,22-dihydroxy compound C, and the compound of medium polarity is identified as 9-hydroxy-3-oxo-4,17(20)-pregnadiene-20-carboxaldehyde (I) as follows. A fraction enriched in the aldehyde (I) is obtained from a preliminary chromatogram on a short silica column eluted with 30% ethyl acetate in methylene chloride. This material (3.3 g) is carefully rechromatographed on three pre-packed Lobar silica-gel columns [size B; E. Merck Co.], arranged in series, and eluted with 20% ethyl acetate in methylene chloride. The aldehyde (I) is obtained as a colorless solid that crystallized as needles (1.05 g) from ethyl acetate/methylene chloride, m.p. 194°–212°, $[\alpha]_D$+96° [c, 1.024; $CHCl_3$].

Analysis: Found: C, 77.53%; H, 8.71%. Calculated for $C_{22}H_{30}O_3$: C, 77.16%; H, 8.83%.

The mass spectrum gave a molecular ion at m/e 342 (base peak) and major fragment ions at 324, 309, 295, 191, 136 and 124.

H-nmr spectrum: 1.02, (18-$CH_3$); 1.36, (19-$CH_3$); 1.82, (21-$CH_3$); 5.88, (4-H); 10.04, (CHO) ppm.

ir spectrum: 3497, 3440 $cm^{-1}$ (—OH); 1663 $cm^{-1}$ ($\alpha,\beta$ unsat. carbonyl); 1622, 1617 $cm^{-1}$ (C=C).

uv spectrum: $\lambda_{max}$ 250 nm; ($\epsilon$, 27,900; methanol).

EXAMPLE 4

By substituting a sterol-degrading microorganism from the genera Arthrobacter, Bacillus, Brevibacterium, Corynebacterium, Nocardia, Protaminobacter, Serratia, and Streptomyces, for *Mycobacterium fortuitum* NRRL B-8119 in the process disclosed for preparing *M. fortuitum* NRRL B-12433, there are obtained mutant microorganisms which are characterized by their ability to selectively degrade steroids with a C-17 side chain and accumulate compound (I) as a major product.

EXAMPLE 5

By substituting the mutants obtained in Example 4 for *M. fortuitum* NRRL B-12433 in Example 1, there is obtained compound (I).

CHART I

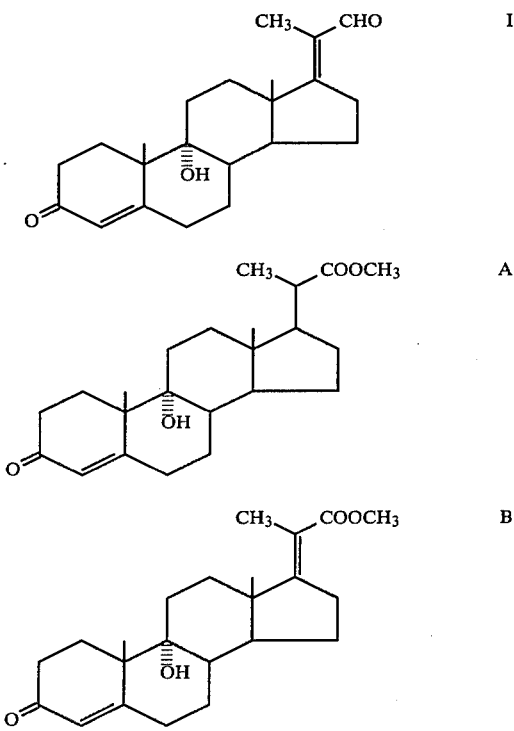

-continued

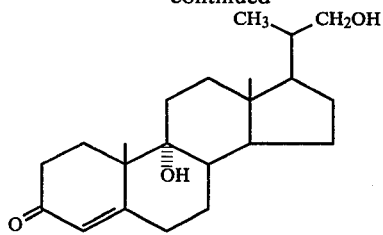
C

We claim:

1. A fermentation process for preparing a compound of the formula

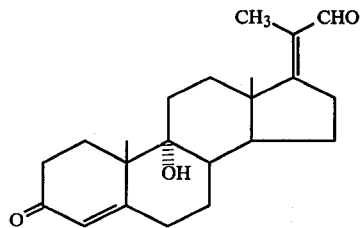
I which comprises cultivating *Mycobacterium fortuitum* NRRL B-12433 in an aqueous nutrient medium under aerobic conditions in the presence of a steroid with a C-17 side chain and recovering the desired product.

2. A process, according to claim 1, wherein said steroid is selected from the group consisting of sitosterol, cholesterol, stigmasterol, and campesterol.

3. A process for preparing a compound, as defined in claim 1, which comprises cultivating *Mycobacterium fortuitum* NRRL B-12433 in an aqueous nutrient medium under aerobic conditions in the presence of a mixture of two or more steroids.

4. A process, according to claim 3, wherein said steroid mixture is selected form the group consisting of sitosterol, cholesterol, stigmasterol, and campesterol.

5. A compound of the formula

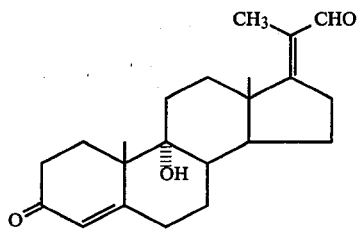
I

* * * * *

UNITED STATES PATENT AND TRADEMARK OFFICE
CERTIFICATE OF CORRECTION

PATENT NO. : 4,425,429

DATED : January 10, 1984

INVENTOR(S) : John C. Knight et al

It is certified that error appears in the above-identified patent and that said Letters Patent is hereby corrected as shown below:

Column 6, Claim 5, lines 15 through 25 inclusive should be deleted.

Signed and Sealed this

Twenty-third Day of October 1984

[SEAL]

Attest:

GERALD J. MOSSINGHOFF

Attesting Officer  Commissioner of Patents and Trademarks